United States Patent [19]

Leahy

[11] 4,386,850
[45] Jun. 7, 1983

[54] CALIBRATION DEVICE AND METHOD FOR AN OPTICAL DEFECT SCANNER

[75] Inventor: Michael F. Leahy, East Brunswick, N.J.

[73] Assignee: RCA Corporation, New York, N.Y.

[21] Appl. No.: 219,515

[22] Filed: Dec. 23, 1980

[51] Int. Cl.³ .................................................. G01N 21/88
[52] U.S. Cl. ...................................... 356/243; 356/237; 250/252.1
[58] Field of Search ............................. 356/243, 237; 250/252.1, 572

[56] References Cited

U.S. PATENT DOCUMENTS 2,364,609 12/1944 Almquist .............................. 356/243
2,936,374 5/1960 Zimmer ............................. 250/252.1
4,236,828 12/1980 Kaneko et al. ...................... 356/243

OTHER PUBLICATIONS

"Reflectivity Reference Standard for Toner Concentration Sensor", Bilby, IBM Tech. Disc. Bulletin, vol. 21, #6, Nov. 1978, pp. 2235-2236.

Primary Examiner—Vincent P. McGraw
Attorney, Agent, or Firm—Birgit E. Morris; Donald S. Cohen; Joseph D. Lazar

[57] ABSTRACT

A calibration device for an optical scanner for optically detecting microscopic defects on object surfaces is formed on a substrate having a characteristic pattern of a plurality of different arrays of artificially created defects. Each array is arranged by size and spacing of the artificial defects to represent an actual defect size. Each artificially created defect of a given array is of the same size. Each defect is provided with a surface which in response to an incident beam of light scatters the light. The response of the system to the scattered light forms a characteristic pattern which corresponds to actual defects.

11 Claims, 13 Drawing Figures

Fig. 3A

Fig. 3B 172 (PATTERN)

| 50/300 | 20/300 | 10/300 |
|---|---|---|
| 1/300 | 3/300 | 5/300 |

5/100 | 3/100 | 1/100

Fig. 3C 178 176 (ARRAY) 174 (DOT) 180

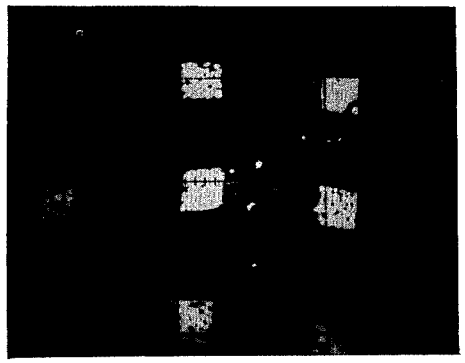
Fig. 4A  (50/300 ARRAY)
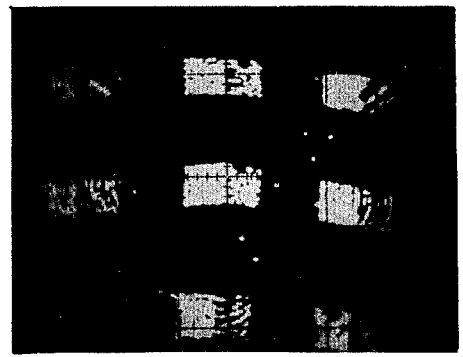
Fig. 4B  (+20/300 ARRAY)
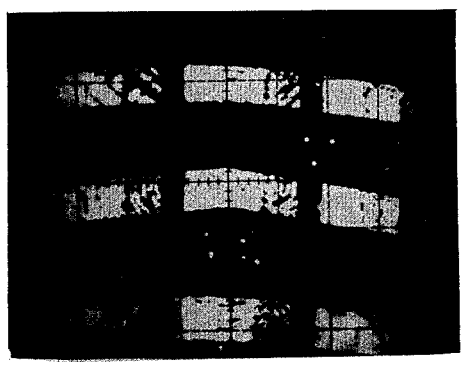
Fig. 4C  (+10/300 ARRAY)
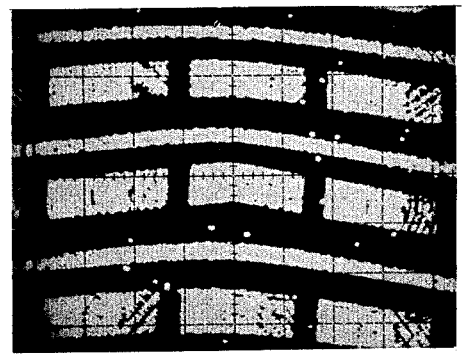
Fig. 4D  (+5/100 ARRAY)

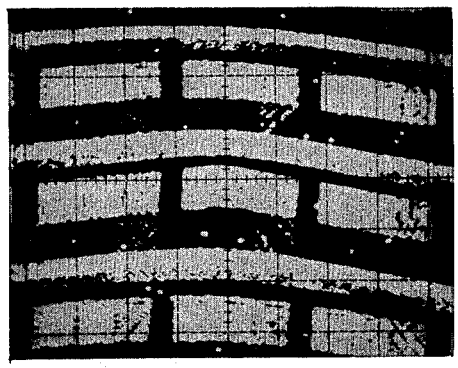
Fig. 4E  (+3/100 ARRAY)
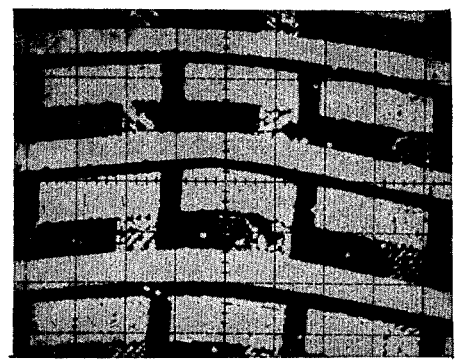
Fig. 4F  (+5/300 ARRAY)
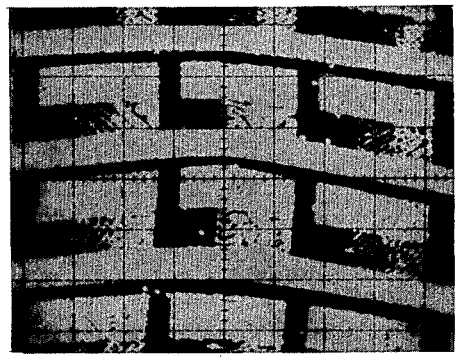
Fig. 4G  (+3/300 ARRAY)
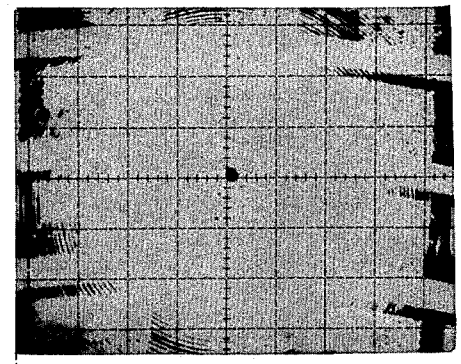
Fig. 4H  (OUT OF RANGE)

CALIBRATION DEVICE AND METHOD FOR AN OPTICAL DEFECT SCANNER

This invention relates to a calibration device and a method for calibrating an optical scanner for detecting microscopic defects by scattered light from the surface of an object.

BACKGROUND OF THE INVENTION

Silicon wafers useful in the manufacture of semiconductor devices require close scrutiny to detect defects as soon as possible in the manufacturing process. Several apparatus are known in the art for detecting microscopic defects on the surface or near the surface of such devices. One such apparatus utilizes a laser beam that is scanned over the surface of a wafer and includes means for detecting scattered radiation from the wafer surface. The specular reflection is blocked from the detection device by suitable arrangement of the lenses and spatial filters. If the surface of the wafer has an imperfection such as dirt, hills, scratches and the like, the laser beam will be scattered from the imperfection. There are also scattering processes such as Raman scattering, etc., which occur, but the intensity due of the light to such scattering effects is usually negligible. The scattered light from the wafer is collected from about the main axis of the lens and is focused on a detector. The scattered light is converted to electrical impulses which can be counted or in the alternative can be displayed as a bright spot on an oscilloscope. See copending U.S. application Ser. No. 000,813, filed by E. F. Steigmeier et al. on Jan. 4, 1979, now U.S. Pat. No. 4,314,763, issued Feb. 9, 1982, entitled "DEFECT DETECTION SYSTEM" for a detailed description of such a scanning apparatus.

It is difficult to calibrate such a scanning apparatus to predictable dimensions of the observed microscopic defects. The usual method for calibrating such an apparatus is to observe the displayed scan by electron or optical microscopic techniques. Such a procedure of calibration is difficult because it is a cumbersome procedure requiring calibration at locations other than where the scanner is located and is more time consuming. There is a need in the art to provide means for calibrating such apparatus quickly and preferably at the site of the apparatus without the use of optical or electron microscopy.

SUMMARY OF THE INVENTION

According to the present invention, a calibration device serving as an object with simulated microscopic defects comprises a semiconductor wafer having a characteristic pattern of a plurality of different arrays of artificial defects. Each array of such defects is formed of a plurality of evenly spaced defects, each defect of a particular array having the same dimension. The pattern of the calibration device when suitably positioned in the machine serves to simulate an object having microscopic defects of unknown dimension when exposed to an incident beam at a preselected intensity value. The calibration device will provide an illuminated pattern that simulates a preselected size of a microscopic defect on the surface of a given object.

BRIEF DESCRIPTION OF THE DRAWING

In the drawing:

FIGS. 3A, 3B and 3C are schematics showing the development of the calibration device according to one embodiment of the invention; and FIGS. 4A–4H are photographs of CRT displays at various preselected threshold adjustments on the scanner apparatus illustrating the calibration displays for a sequence of predetermined defect sizes.

DETAILED DESCRIPTION OF A PREFERRED EMBODIMENT

Figure 1:
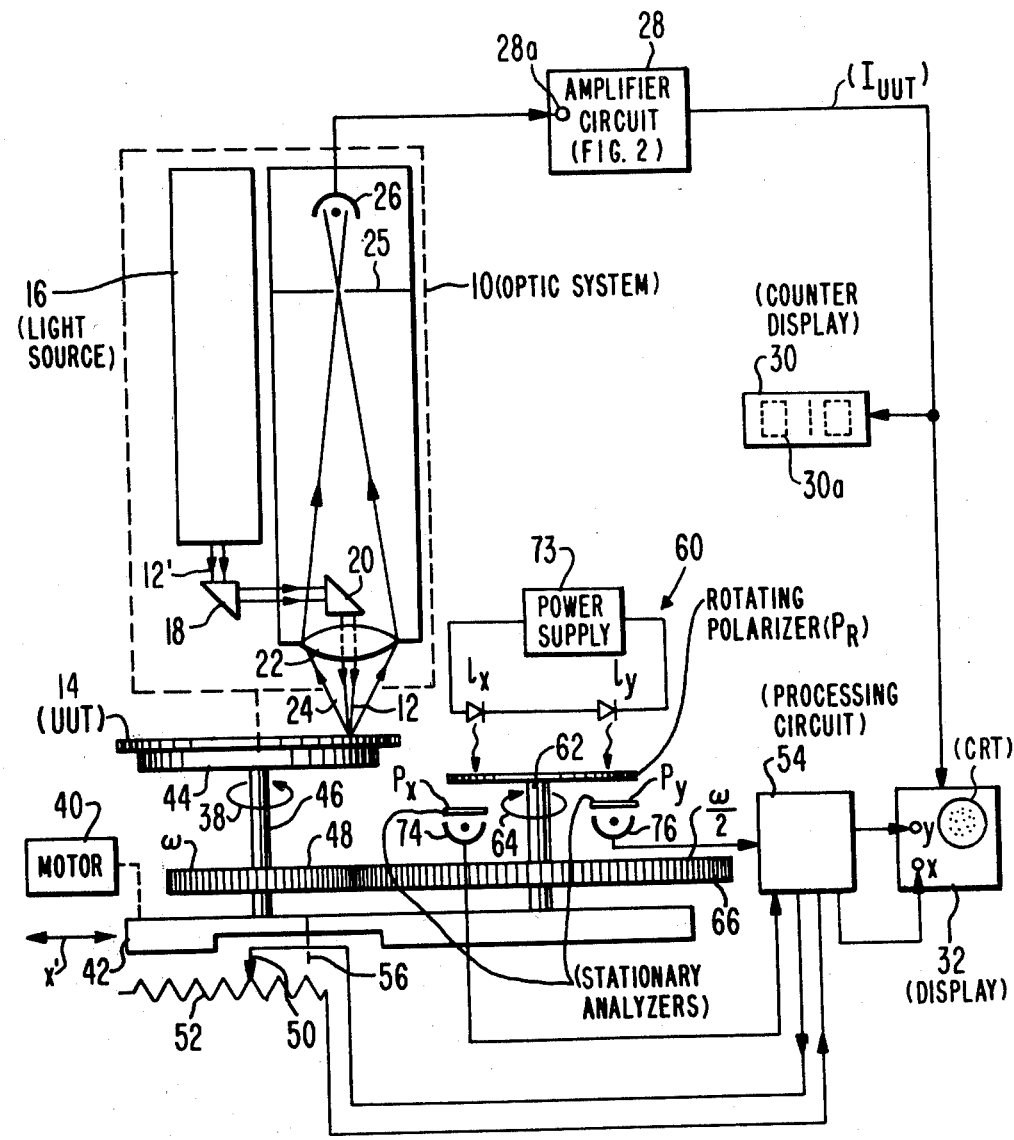
FIG. 1 is a schematic of an optical scanner apparatus for use in practicing the invention.

Before proceeding to a detailed description of the calibration device of the invention, reference is made to FIG. 1 illustrating a suitable optical scanner for which the calibration device is used. The apparatus shown in FIG. 1, described in detail in the above-identified application, comprises an optical system 10 which includes a light source 16 providing a beam of light 12' passing through a series of prisms 18 and 20 and then through a focusing means, such as lens 22, providing beam 12. The light source 16 provides a light of any selected wavelength and includes light in the infrared (IR), visible or ultraviolet (UV) light spectrum. Light source 16 may be a low power laser, for example, a HeNe laser producing light at 6323 angstroms in wavelength which is focused by lens 22 into a spot 250 $\mu$m in diameter. Beam 12 of the laser light is projected onto the surface 14 of an object such as the unit under test (UUT). The unit under test may be a wafer of silicon as used in the manufacture of integrated circuits (IC) and other semiconductor devices. The position of the light source 16 is not critical, but the position of the beam 12 between the prism 20 and object surface is important. The axis of the beam is preferably substantially perpendicular to the surface 12. Light generated by laser 16 is scanned over the surface 14 of the UUT and is reflected back through the lens 22 via beam pattern 24 and collected on a photodetector 26 which is positioned along the axis of the beam 12. Lens 22 serves a first of two spatial filters to specular reflected light along the axis of beam 12. The defects that appear on the surface 14 of UUT may be as small as 1 $\mu$m in area. A defect may extend beyond the diameter of the laser beam, namely beyond the 250 $\mu$m, in which case its shape, as distinguished from its mere size, will be detected by the scanning process. Surface defects scatter a sufficient amount of light beyond prism 20 so as to be detected by detector 26.

A defect for the purposes of this description shall mean any imperfection to an ideally optically flat surface or in the underlying structure below the surface of the object under test. An imperfection to the optically flat surface includes particulates (dust, etc.) nicks, hills, scratches, depressions, etc., which are detected when there is little or no penetration of the incident light. An imperfection in the underlying structure includes inclusions (foreign particles), bubbles in the form of voids, microcrystalline grain boundaries, etc., which are detected when there is substantial penetration of the incident light. The depth of penetration is a function of the wavelength of light and the material. In general, since an optically flat surface, will not scatter light, the defect will have surface portions that are not optically flat with respect to the incident light.

An aperture mask 25 acts as the second of two spatial filters in optical system 10 and prevents ambient light from being projected onto the detector 26. The output of detector 26 is applied to an amplifier circuit 28 which provides an output signal to either or both a counter display 30 or a cathode ray tube (CRT) display 32. Counter 30 counts the number of defects that are detected during a scan of beam 12. The CRT display 32 provides a visual display of the relative spatial distributions of the locations of the defects on the UUT. Amplifier 28 is analogue in nature and produces an amplified output of the detector output proportional to the input signal it receives from detector 26 at terminal 28a. This results in gray scale in the display 32, the intensity of the indications of defects on the CRT screen being indicative of the defects. A more detailed schematic of amplifier 28 is shown in FIG. 2 to be described.

In the form of the scanner shown in FIG. 1, the beam 12 scans the UUT in spiral fashion and the electron beam of the display 32 is also scanned in spiral fashion. The UUT may be a circular surface and for such purposes a spiral pattern is useful. If desired, the pattern may be converted into a X-Y display which is achieved by the coordinate transformation system 60 which transforms polar coordinates of the beam striking at surface 14 into suitable rectangular coordinates which are applied as X-Y coordinate inputs for the display 32. A detailed description of the polar coordinate system is not given here, but for a more detailed description see the above-identified copending application Ser. No. 000,813, described above and hereby incorporated by reference. In brief, the coordinate system includes a polarizer $P_R$, spaced, stationary analyzers $P_y$ and $P_x$, detectors 74 and 76 excited by the photocells $L_x$ and $L_y$ which are energized by power supply 73. The system 60 includes a shaft 62 rotating in direction 64 over table support 42 slideable by motor 40. A gear 66 connected to shaft 62 is meshed with gear 48 so that the polarizer $P_R$ rotates at a predetermined angular speed, typically one half the angular speed of the UUT on table 44 rotated by shaft 46 in direction 38. The light from the diodes $L_x$ and $L_y$ are passed through the polarizer $P_R$ and detected by detector 74 and 76 and applied to the processing circuit 54. A wiper arm 50 is connected (dashed line 56) to the table 42 and moves with the table 42 as the table translates in the direction x'. The wiper arm 50 is part of a potentiometer 52 which is connected to processing circuit 54 for position control purposes. The processing circuit 54 provides the X and Y signals for application to the CRT 32 in the manner described in the above-identified application.

In operation, when the incident beam 12 is positioned at the center of UUT, the output of amplifier 28 is zero. As the beam 12 is moved from the center, signals are detected by detector 26 and applied to amplifier circuit 28 and applied to display 32. The display is scanned in an X-Y direction, providing a visual display corresponding to the scattered reflections from the beam 12. The display appears as bright spots and positions of the spots on the display screen correspond to the spatial distribution of the locations of the defects on or close to surface of the UUT.

Figure 2:
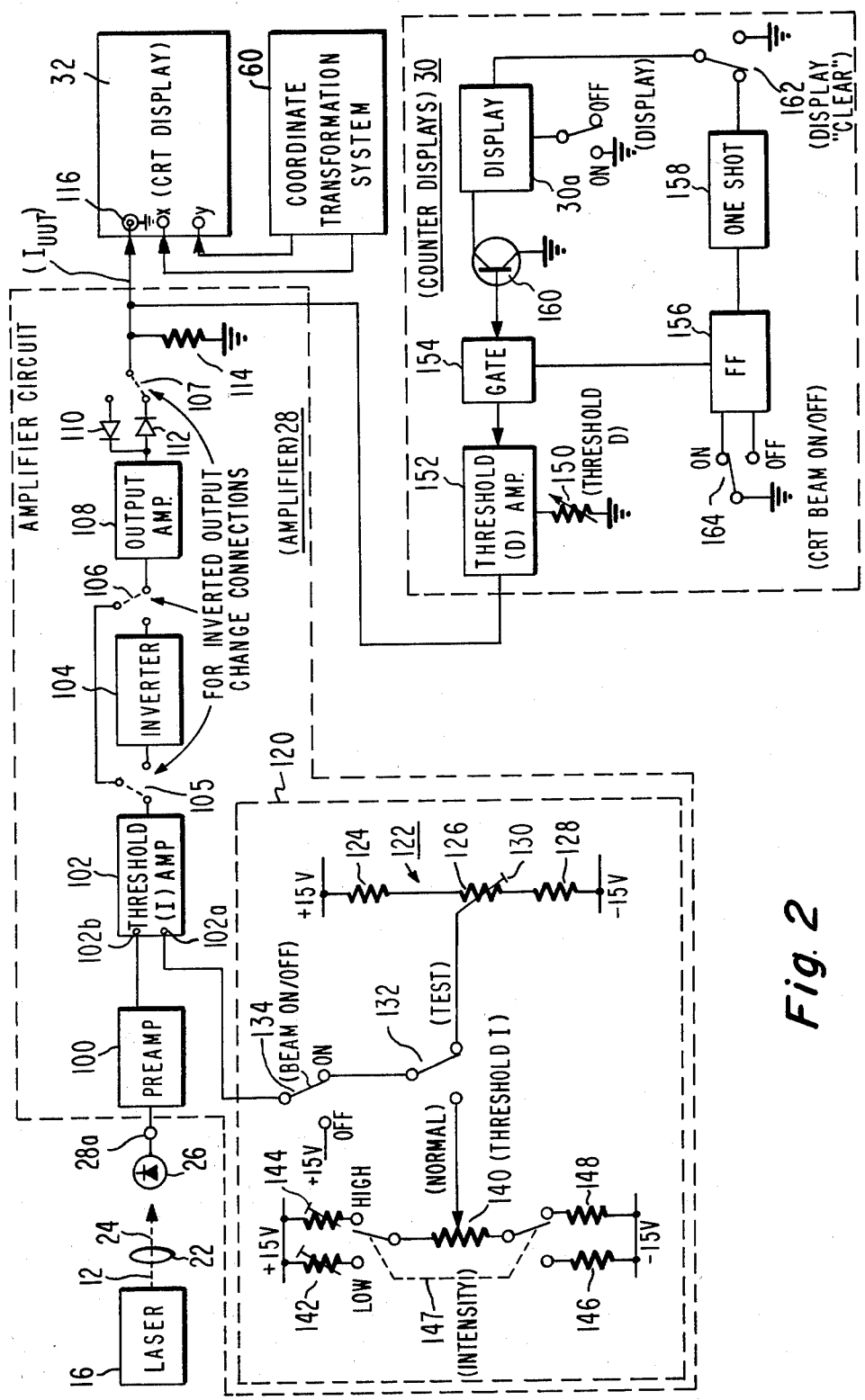
FIG. 2 is a block schematic of the amplifier circuit of the scanner illustrated in FIG. 1.

Reference is now made to FIG. 2, which shows particularly the amplifier circuit 28 in relation to other portions of the system. Laser 16 provides a fixed intensity beam 12 which is scattered as beam 24 which in turn is detected by detector 26. The output of detector 26 is coupled via terminal 28a to a preamplifier 100 which in turn is coupled to a threshold current amplifier 102 and thence to single pole, double throw switch 105 and eventually switch 106. The threshold signal from amplifier 102 is either applied directly to an inverter 104 or, in the alternative to an output amplifier 108. Single pole, double throw switch 107 inserts either one of diodes 110 or 112 in the circuit depending upon the insertion or removal of inverter 104 by switches 105 and 106. Inverter 104 is used, if desired, to invert the output signal of amplifier 102 whereby the display of a detected defect will be inverted. Output resistor 114 connected to ground provides the output signal which is applied to the cathode of the CRT 32, as at terminal 116.

A threshold control network 120 provides a means for controlling to a predetermined or preselected value the intensity I of the beam of the CRT display 32. The network 120 comprises a reference potentiometer 122 formed of serial resistors 124, 126 and 128 connected between +15 volts and −15 volts. An adjustment tap 130 is connected to one terminal of a single pole, double throw switch 132, the common terminal of which is connected to another switch 134 and thence to the input 102a of threshold amplifier 102. This provides in a test mode an adjustable voltage to the threshold I amp 102 to provide a test signal for display on the CRT display 32. Theshold amplifier 102 is a suitable operational amplifier having a first input 102b and a second input 102a. The network 120 with the switches 132 and 134 in the position as shown provides a control voltage to terminal 102a of amplifier 102 as the test mode of operation during which the laser is scanning the UUT or calibration wafer. For normal operation to preset the predetermined threshold at which the CRT beam provides a predetermined intensity I, a threshold intensity adjustment potentiometer 140 is connected by ganged switch 147 between either one of a pair of selectable resistors 142 and 144 connected in common to +15 volts, the other terminals being connected to switch 147 through a pair of resistors 146 and 148 to −15 volts. The resistors can be selected to provide different voltage ranges to thereby change the intensity of the CRT beam over a wide range of values as desired. In operation, with switches 134 and 132 positioned to the "normal" position opposite to that shown in FIG. 2, the intensity threshold (I) control 140 will be in the circuit. By adjusting potentiometer 140, the intensity (I) of the CRT beam may be adjusted to a predetermined value. Suitable calibration indicia on the potentiometer are provided (not shown) as a repeatable reference of the selected position of the potentiometer 140.

In addition to the threshold (I) intensity control network 120, a second threshold (D) control 150 is provided to modify the intensity signal ($I_{UUT}$) applied to the terminal 116 of CRT 32. The D threshold adjustment 150 provides a reference adjustment of a threshold amplifier 152 whose input is coupled to the output of a gate 154 which in turn is triggered by flip-flop 156 responding to one shot 158. Gate 154 is coupled to transistor 160 which in turn is coupled to counter 30a of display 30 shown in FIG. 1. With momentary contact switch 162 normally in the position shown, triggered events will register in the display 30 and with the switch 162 momentarily in the other position the display 30 is cleared to "0000". Switch 164 is a switch for controlling the CRT beam 12 to be "on" or "off" in accordance with the position as shown. The coordinate transformation system 60, described above for FIG. 1, is shown in block form coupled to the terminals X and Y of the CRT scope display 32 to provide the X-Y display pattern described above.

Thus, the threshold intensity (I) potentiometer 140 and threshold (D) potentiometer 150 provide an adjustable detection sensitivity control of the scattered light. The sensitivity of detection can be further increased by changing the gain of the amplifier 108. The intensity of the CRT display beam is adjusted by the threshold I potentiometer 140 to increase the detector signal sufficiently to the level at which the CRT 30 displays the detected signal.

In operation with a UUT in position on the table 44, the scanner provides a beam 12 which in turn provides a scattered beam 24 which, after detection, will provide a display on CRT 32. Defects that may appear will be counted and displayed in counter display 30. However, there is difficulty in calibrating the apparatus so that the dimensions of the defect are known. Opitcal or electronic microscopic techniques have heretofore been used to determine the dimensions of such defects.

Figures 3A, 3B, 3C:
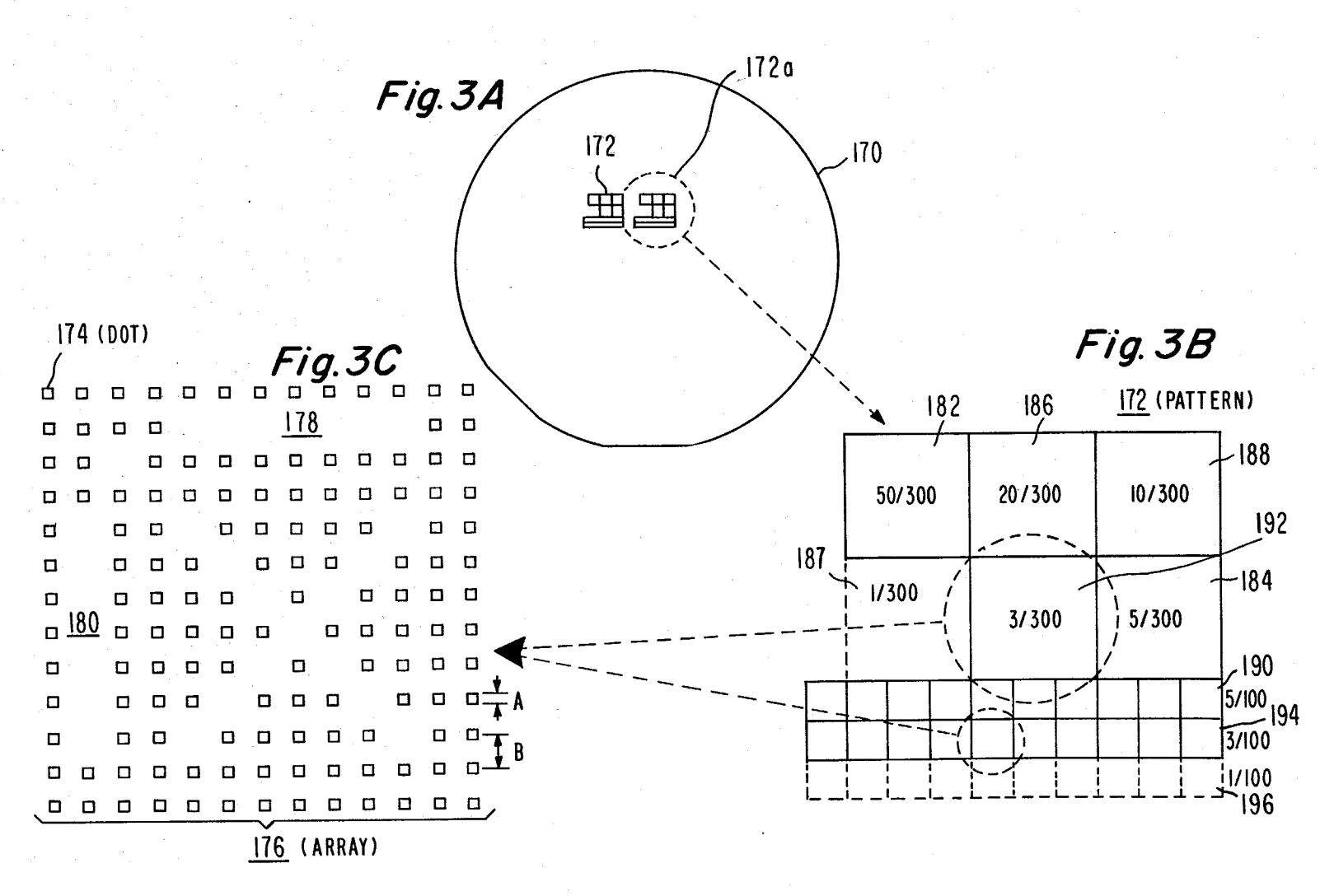

A calibration device 170 of the invention is illustrated in FIG. 3A. The calibration device 170 is suitably formed on a wafer in which a plurality of patterns 172 are provided in the form of a plurality of artificial defects such as islands of dots 174. In the alternative and preferred form, dots 174 are etched into the surface of the wafer as will be described further. In brief for the present purposes, it should be understood that the response of the scanner will be different for different types of surface defects. For example, a dust particle with a very rough and irregular surface, would probably scatter more light than a smooth surface such as a surface exhibited by a latex sphere of the type used in the art to calibrate an electron microscope. Conversely, a pit developed by etching might scatter very effectively due to off-axis specular reflection from the etched surfaces. It is for this reason that the preferred embodiment of the invention provides for the dots in the form of etched pits rather than islands of deposited materials. Dots in the form of islands tend to be quite smooth particularly with vertical walls and flat surfaces that do not scatter well. Since the calibration device 170 of the invention serves to simulate an actual microscope defect on the surface of UUT, it is important that the scattered light from the artificial defects of the calibration device provide an intensity of the reflected beam that approximates if not equals the scattered light intensity from actual defects. It should be noted that specular reflections are very strong as compared to scattered light. Moreover, an off-axis specular reflection is much stronger than off-axis scattered light. Nevertheless, it should be appreciated that, in this environment, there are many types of defects seen which all scatter with different effectiveness.

The patter 172 of dots 174 shown in FIG. 3C is suitably developed on the wafer 170 by a mask and known photolithographic techniques. A suitable mask making procedure such as a manufacturing electron-beam system (MEBES) is used. Each of dots 174 serve as the fundamental artificial microscopic defect from which the scattering of the light emanates. Each dot 174 is essentially a square on the wafer surface 170 and can be defined in any appropriate material such as silicon dioxide ($SiO_2$) or silicon (Si). The dots 174 are arranged into an array 176 of a group, for example, of 13 by 13 dots 174. The number of dots in an array must be large enough to form a visible pattern on the CRT display 32. If the array 176 was formed of too few a number of dots 174, for example, four dots, the observed pattern would not be distinctive enough to be unambiguous as compared to other four-dot patterns representing a different calibration size. Some of the dots can be omitted from the array 176 as indicated by the omitted portions 178, 180, etc., in FIG. 3C. The missing dots are useful in providing a means for identifying an array within the pattern or orientation of the array or pattern in the display. Furthermore, a pattern of missing dots can be arranged to depict the numbers 5, 10, 20, etc., depicting thereby the calibration size of the particular array within the pattern 172. The dots 174 which make up or form an array 176 may be of various side dimensions ranging from 50 microns to 1 micron.

In general, there are two types of arrays 176. In one form of the array, dots 174 are spaced from each other on 300 micron spacing centers. In the other form of the two arrays dots 174 are spaced on 100 micron centers. Arrays on 300 micron centers are formed of dots having a side dimension of 50, 20, 10, 50, 3 or 1 micron. The arrays formed of 100 micron-spaced dots 174 are provided with either 5, 3, or 1 $\mu$m dots. For purposes of this description an array of 50 micron dots on 300 micron centers may be called a 50/300 array as indicated by array 182 of the pattern 172 shown in FIG. 3B. Similarly, 5 micron dots 174 on 100 micron centers may be called a 5/100 array represented by array 190 of FIG. 3B. The arrays 182, 184, etc. are arranged into a pattern 172 as shown in FIG. 3B and shown within the circle 172a of FIG. 3A. The patterns 172 are repeated across the entire surface of the wafer 170. Masks are suitably provided to provide a 4" mask set on a 3" wafer for example. The calibration device 170 was developed on bulk silicon wafers which have grown on them a layer of silicon dioxide about 2000 angstroms thick. The plurality of patterns 172 was defined in the oxide film with standard wet chemical techniques. Patterns may also be generated directly on a surface of bulk silicon wafers by plasma etching. In the preferred form of pattern development, etched pits are formed into the surface of the wafer 170. As indicated above, the pits of each of the dots 174 scatter more light than the islands of silicon dioxide forming dots 174 and simulate better than normal type of surface contamination. Wafers have been made in the form shown in FIG. 3B but without a 1/300 array 186, namely, without a pattern of dots 1 $\mu$m in diameter on 300 $\mu$m centers. However, a calibration device including array 186 can be made within the state of the art of etching and mask manufacture. Such a calibration device will accordingly provide resolution down to 1 micron defects. Nevertheless, devices made with arrays with 3 to 50 micron dots are still very effective in detecting defects of concern to the semiconductor industry. It will be noted, as shown in FIG. 3C, that dimension A represents the dimension of each individual dot 174 whereas dimension B represents the spacing between the dots, as described hereinabove.

In operation, the scanner is aligned as necessary as described in the aforementioned co-pending application, now U.S. Pat. No. 4,314,763, and the calibration wafer 170 is placed on the table 44. If it is desired to provide an output for display by counter 30 only, the threshold D adjustment 150 (FIG. 2) is set to a predetermined value, nominally half of the full scale of the potentiometer. The potentiometer 140 for the intensity threshold I with the switches 132 and 134 in the left position from that shown in FIG. 2 is adjusted to give a maximum count on the display 30. A distinct maximum will be observed representing a counting of all of the light scattering dots 174 on the wafer 170.

If a CRT output display is desired, the CRT 32 may now be calibrated for optimum response by increasing the CRT intensity control (not shown) until a similar display to that shown in FIG. 4G (to be described further hereinafter) is obtained. The response of the CRT display 32 and the counter 30 should now be equivalent. That is to say, any count of defects (as defined above) that were scanned and detected to provide a count will also appear as a visual display of a sequence of spatially displaced spots on the CRT display 32. To set the response of the scanner to be sensitive to a particular size of microscopic defect, the threshold I potentiometer 140 should be set to a minimum or zero value and the wafer 170 scanned. Some defects may be observed even at this low setting. The potentiometer 140 (threshold I) is increased until a portion of the array 176 of squares is seen. FIG. 4A illustrates such a display. The photographs of FIGS. 4A–4G are, it is to be noted, full size photographs as seen by an operator viewing a typical CRT display. One advantage of the calibrator of this invention is the ability of an operator to visually observe a pattern and determine from the observed pattern the size of the defect. The portion of the arrays 176 as seen in FIG. 4A are the portion of pattern 172 represented by block 182 only of FIG. 3B. As the threshold (I) potentiometer 140 is adjusted to increase the sensitivity of the detection system, the next display from the calibrator device 170 will be the 20/300 array represented in FIG. 3B as array 182 plus array 186. Thus, array 182 is still displayed and, in addition, the array 186 appears alongside the array 182. It should be understood that the individual dots 174 in each of the arrays 182 and 186 are not actually seen in the display although there may appear to be a regular omitted-dot pattern in the array such as portions 178 and 180 of array 176, FIG. 3C. The area of the missing dots represented by portions 178 and 180 of FIG. 3C can at times be seen with appropriate adjustment of the CRT. Increasing the threshold (I) potentiometer 140 still further will result in the observation of either the 10/300 array 188 or the 5/100 array 190, as illustrated by FIGS. 4C and 4D, respectively. Note that arrays 190, 194, 196 are repeated 10 times each within the pattern 172 as seen in FIG. 3B.

The diameter of laser beam 12 is nominally 250 $\mu$m as explained above and the response to the 5/100 array 190 is greater than the response to the 10/300 array 188, simply because more scattering centers manifested by the dots 174 are within the beam 12 at a single instant in the closely-spaced 5/100 arrays 190.

The next array of the pattern to appear with further increase of the threshold intensity (I) potentiometer 140 is the 3/100 array 194, which appears as a doubling of the width of the 5/100 arrays 190. This display is shown in FIG. 4E. The calibration procedure is continued until the 5/300 array 184 (FIG. 4F) and the 3/300 array 192 (FIG. 4G) become visible on the display 32. The 5/100 bar pattern 190 is seen in FIG. 4D. The double bar pattern of 190 and 194 is seen in FIG. 4G. A device can be made, but not shown in the photographs, with arrays of 1 $\mu$m dots on 100 $\mu$m centers represented in dotted lines by bar pattern 196 shown in FIG. 3B.

By noting the various settings of the threshold I potentiometer 140 at which the various arrays illustrated by FIGS. 4A through 4G appear in the display, the sensitivity of the apparatus may be adjusted to respond to any desired dimensional range of defects. It is possible that all of the arrays 176 would not be seen before the signal is washed out by noise and surface scattering from the silicon surface even in places where there are no microscopic defects or other features. Since the mask forming the calibration device 170 incorporates some blank areas such as portions 178 and 180 (FIG. 3C), this washing out effect can be observed from the CRT display 32. However, these portions are not easy to observe. The areas of arrays 187 (1/300) and 196 (1/100), can be used to observe the washing-out effect. Even if such arrays are not used, the area to the left of the array 182 (50/300) and array 187 (1/300) could be used for such purposes.

As mentioned hereinabove, it is preferred that the dots forming the artificially created defects, causing the fundamental source of scattered light, be in the form of a recess in the general form of a square and an etched surface within the recess. In systems in which the dots 174 were in the form of islands, the correlation of the response characteristics of the artificially created defects of a specific size to the response characteristics of actual defects of the same or similar size was less than fully satisfactory. Microscopic evaluation of the structural features of the island form of dots shows vertical sidewalls and a smooth top surface. Any scattering comes from only the edges of the silicon dioxide island and, as such, the island reponds as if it were a much smaller defect thereby disqualifying the desired simulation of an actual microscopic defect or particle of the same dimension. The material used for the island may also have an effect. The preferred choice of silicon dioxide is made on the basis of durability and ease of patterning, but the wafers 170 could be fabricated with any suitable semiconductor material. It is possible to choose a surface which could be matched in scattering response to typical ambient contamination. For example, the user will empirically determine what kinds of contamination are likely to be encountered, and attempt to match the scattering efficiency of like-sized artificial defects to the scattering efficiency of that contamination. Examples of such materials might be photoresists, polycrystalline silicon, or metals. In the preferred form, a selective etch to form pits in <100> silicon would be a reasonable choice resulting in a faceted pit which might be expected to scatter very effectively.

It will now be appreciated that the calibration device described above provides a means to calibrate optical scanners useful in detecting defects in semiconductor materials without the use of any other calibration equipment. The pattern of the device is constructed such that the response of the scanner to micron sized particles can be visualized on a macroscopic scale in the order of 1 cm as seen in FIG. 4A, for example. The pattern is constructed of arrays of surface features with typical sizes ranging from 1 to 50 microns in such a way that the scanner will respond to individual features of the pattern. When this occurs, the individual features combine to form a macroscopic pattern of artificial microscopic defects on the display. Adjustments of the sensitivity of the scanner by potentiometer 140 to display the various features of the pattern is used as a means to calibrate the scanner. In this way the scanner is unambiguously calibrated to a particular sensitivity. Thus, the scanner when calibrated allows the operator to observe a defect and determine the size thereof to a reasonable degree of accuracy by noting the adjusted value of potentiometer 140 at which the defect was displayed. This potentiometer value is compared to the calibration values as described above.

While the artificially created defects simulate defects that occur in or on the semiconductor substrate, it should be understood that the accuracy of the wafer is dependent on the degree of scattering that is effected by the individual and combined defects. What is essential is that the artificially created defect scatters light rather than manifests only simple on-axis specular reflection.

The calibration device described may be arranged in any desired form other than that illustrated above. In practice, the calibration device 170 is used to quickly adjust potentiometer 140 of the laser scanner to, for example, an acceptable threshold value for grading production wafers. If the acceptable quality of wafers is one, for example, having defects not greater than 20 $\mu$m, the scanner is adjusted to provide an output corresponding to FIG. 4B. Wafers are screened accordingly.

What is claimed is:

1. A calibration device for a system of the type for visually detecting microscopic defects in a certain specularly reflecting surface of a given object, said system comprising first means for scanning said reflecting surface with an incident beam of light that illuminates a relatively small spot area of said entire reflecting surface area, which spot area is large relative to the area of any microscopic defect, the incident beam of light being directed to said surface illuminated by the incident beam of light is detected substantially independently of light specularly reflected from the same surface, and a second means for varying the threshold of detection of the scattered light, wherein said calibration device service as a reference object with artificially created microscopic defects comprises:
    a substrate having a characteristic pattern of a plurality of different arrays of artificial defects,
    all of the artificial defects of a particular array being of the same size and being evenly spaced from each other,
    each artificial defect being provided with a surface, which, in response to an incident beam of light of said system at a preselected intensity, scatters the incident light to provide together with a predetermined plurality of adjacent artificial defects a visually observable pattern corresponding to actual microscopic defects of a known dimension.

2. A calibration device according to claim 1 wherein said artificial defects are in the form of islands of material formed on the surface of said substrate.

3. A calibration device according to claim 1 wherein each of said artificial defects is a recess formed in the surface of said substrate.

4. A calibration device according to claim 1 wherein said artificial defects are generally square, each square having a side length selected from one of the dimensions 1, 3, 5, 10, 20 and 50 $\mu$m.

5. A calibration device according to claim 4 wherein said squares in a given array are evenly spaced by either 100 or 300 $\mu$m.

6. A calibration device according to claim 1 wherein each array of artificial microscopic defects forms a square.

7. A method for calibrating a system of the type that optically detects microscopic defects in a certain specularly reflecting surface of a given object, wherein said method comprises the steps of:
    forming on a substrate a calibration device having a characteristic pattern of a plurality of different arrays of artificial microscopic defects,
    all the defects of each array being of the same size and being evenly spaced from each other,
    a predetermined adjacent plurality of said artificial defects representing a visually observable pattern corresponding to actual microscopic defects of a known dimension;
    scanning said pattern with a beam of light of said system having a given spot size, and
    detecting scattered light reflected from the illuminated pattern and generating an electrical signal representing the scattered light from said pattern, the magnitude of the electrical signal being indicative of the sensitivity of said system.

8. The method of claim 7 comprising further forming each artificial defect in the form of an island of material on said substrate.

9. The method of claim 7 comprising further forming each artificial defect in the form of a recess on said substrate.

10. The method of claim 7 comprising further arranging the pattern with certain arrays having artificial defects spaced apart a greater distance than the scanning beam size and other arrays having artificial defects spaced apart a smaller distance than the scanning beam size.

11. The method of claim 7 further comprising the step of providing in response to the electrical signal a visual display on a CRT, and
    adjusting the threshold of detection of the system during each scan to provide a visual display of scattered light manifesting a microscopic defect of known dimension, the adjusted value of the threshold being thereby a calibration of the system for defects of similar visual appearance.

* * * * *